United States Patent [19]
Glassman

[11] Patent Number: 5,899,878
[45] Date of Patent: May 4, 1999

[54] NASAL IRRIGATION SYSTEM

[75] Inventor: Daniel Glassman, New York, N.Y.

[73] Assignee: Bradley Pharmaceuticals, Inc., Fairfield, N.J.

[21] Appl. No.: 09/103,849

[22] Filed: Jun. 24, 1998

[51] Int. Cl.⁶ .................................................. A61M 31/00
[52] U.S. Cl. ............................ 604/48; 604/19; 604/54; 604/73; 604/275; 604/902; 433/95
[58] Field of Search .................................. 604/48, 19, 54, 604/73, 80, 94, 93, 131, 264, 173, 257, 275, 285, 902; 433/25, 91, 95, 96

[56] References Cited

U.S. PATENT DOCUMENTS 3,847,145  11/1974  Grossan .
5,788,683   8/1998  Martin ..................................... 604/319

OTHER PUBLICATIONS

M. Grossan, "A Device for Nasal Irrigation", American Academy of Ophthalmology and Otolaryngology, vol. 78, Jul.–Aug. 1974, No. 4, pp. ORL–279.
R. Talbot et al., "Mucociliary Clearance and buffered Hypertonic Saline Solution", *the Laryngoscope*, 107: Apr. 1997, pp. 500–503.
"RhinoCare™ Nasal Douche" brochure, Siemens & Co. GmbH & Co. KG (approximately 1990).

*Primary Examiner*—Wynn Wood Coggins
*Assistant Examiner*—N. Kent Gring
*Attorney, Agent, or Firm*—Merchant, Gould, Smith, Edell, Welter & Schmidt, P.A.

[57] ABSTRACT

There is disclosed a nasal irrigation system having an applicator or irrigating member through which a pressurized stream of irrigating fluid is passed through to the nasal passage. The applicator or irrigating member includes a tubular member, adapted for receiving a pressurized stream of fluid from a fluid source, having a bore extending therethrough. The tubular member is formed of a first portion and a second portion offset at an angle from each other. One portion of the tubular member includes an opening extending into the bore. The covering and uncovering of the opening by the user allows for the user to control the pressure of the fluid stream through the irrigating member, such that the fluid stream is directed to the nose and nasal passages when desired. A fitting is attached to an end of the tubular member for further comfort for contacting the nose. A method for using the irrigating member and the system including this irrigating member is also disclosed.

15 Claims, 3 Drawing Sheets

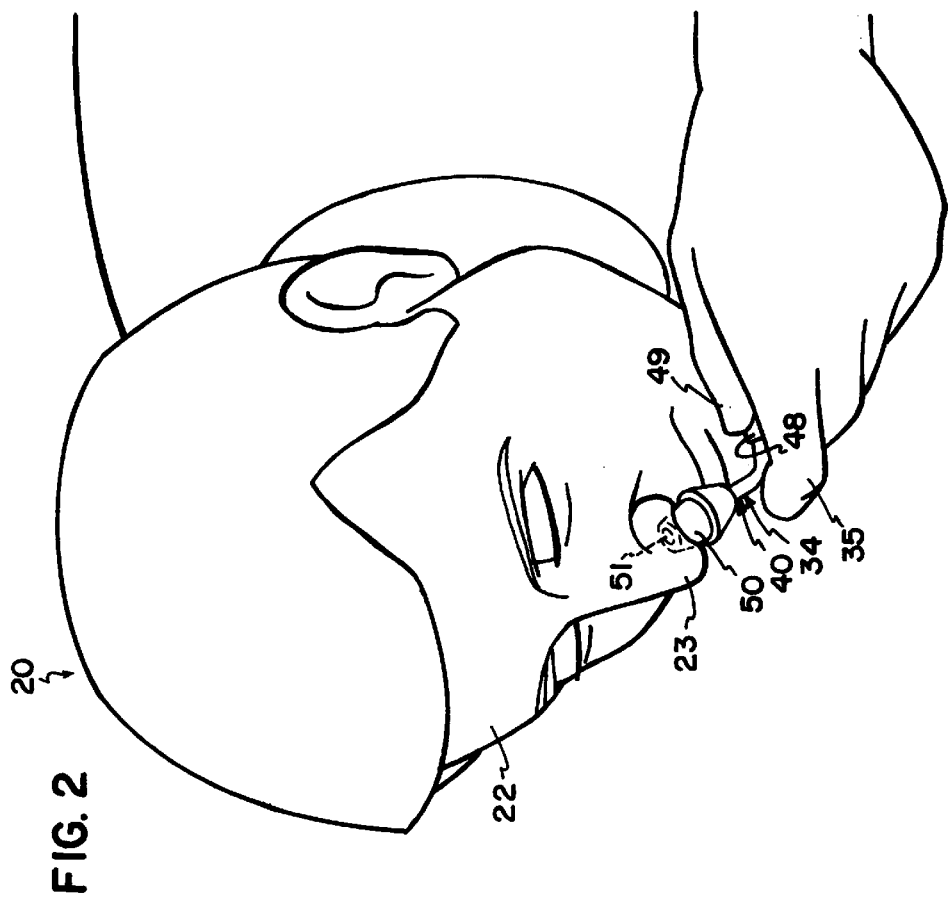
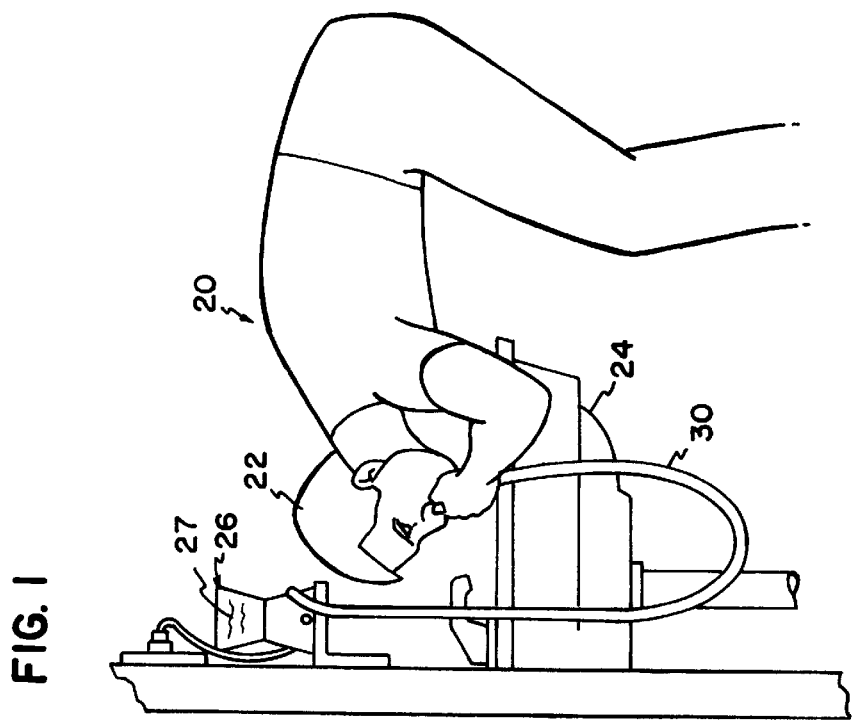

NASAL IRRIGATION SYSTEM

FIELD OF THE INVENTION

The present invention is directed to a device for nasal irrigation, and in particular to a device for nasal irrigation that allows the user to control the flow of irrigation fluid therethrough.

BACKGROUND OF THE INVENTION

Sinusitis is caused by inflammation in the nose. This can be due to a variety of factors, including any combination of inhaled allergens, inhaled pollutants including tobacco smoke, infectious agents (including viruses such as those that cause the common cold and bacteria) abnormalities in the structure of the nasal passages, and reflux of stomach acids. As a result of these factors, the membranes lining the nasal cavity can become swollen and are unable to function properly. Sinus and nasal mucus can not be cleared, sinus cavities become clogged, and normal breathing is inhibited. In addition, bacteria can begin to grow rapidly in the accumulated sinonasal mucus, leading to sinus infections, which are potentially serious and even fatal diseases.

Accordingly, it is highly desirable to irrigate the nasal passages, to aid in the clearance of secretions, debris, intranasal crusts, and other intranasal irritants, and keep the nasal passages clear. This irrigation inhibits the chances of sinusitis, infectious processes, and other sinonasal conditions.

U.S. Pat. No. 3,847,145 (Grossan) discloses one such system, through which the nasal passages may be irrigated. The system includes a device that receives fluid from a fluid source, typically in a pulsatile mode under pressure, and transfers this fluid through a hose to an applicator, through which the fluid enters the nose (nostril) when the tip of the applicator is placed proximate thereto. This system exhibits several drawbacks.

Initially, the applicator is uncomfortable to use, for the user must position their fingers on a small fingertip grip. Additionally, the applicator lacks any structure thereon from which the user can control fluid flow therethrough. Accordingly, should the user suddenly desire to cease fluid flow to the nasal passages, the applicator must be removed from the nose, resulting in fluid squirting in all directions in an uncontrolled manner, until the device can be accessed and the fluid flow controlled, by adjusting a control mechanism or the like. In the interim time period, this uncontrolled squirting makes a mess of the surrounding area. Similarly, even a controlled cessation of the fluid flow, even if temporary, must be done by adjusting a control mechanism on the device itself. This requires the user to either leave the downwardly bent position, to properly reach the control mechanism on the device, such that fluid may fall outside of the basin, or remain in the downwardly bent position and attempt to reach the control mechanism on the device and risk potentially bumping or knocking the device, whereby it may be damaged.

Finally, the applicator of Grossan was designed to be held at a gripping portion, such that when the applicator was pressed into contact with the nose, a torque was created on the clear plastic tube, causing it to bend and subsequently break. Breakage typically occurred at the junction of the tube and the gripping portion.

SUMMARY OF THE INVENTION

The present invention overcomes the problems associated with the prior art by providing a device, including an applicator or irrigating member that is comfortable in the hand of a user and that includes structure thereon, from which the user can control fluid flow therethrough, and thus have sufficient control over the instant nasal therapy. The applicator or irrigating member comprises a tubular member, adapted for receiving a pressurized stream of fluid from a fluid source, having a bore extending therethrough. The tubular member is formed of a first portion and a second portion offset at an acute angle from each other. One portion of the tubular member includes an opening extending into the bore. The covering and uncovering of the opening by the user allows for the user to control the pressure of the fluid stream through the irrigating member, such that the fluid stream is directed to the nose and nasal passages when desired. A thumbrest is slidably attached to the portion of the tubular member that includes the opening. A fitting is attached to an end of the tubular member for further comfort in contacting the nose.

The thumbrest is such that it can be slid along the tubular member to a position proximate to the opening. When the user places his thumb on the thumbrest, the user's index finger naturally follows the thumb, to a position where the index finger easily maneuvers to cover and uncover the opening, controlling the pressure of the irrigation fluid stream traveling through the applicator. With the thumb and index finger holding the applicator at the tube, torsional forces on the tube, created when the applicator, and specifically the fitting is placed into contact with the nose, are minimized, thus, the chances for tube breakage, and in particular breakage at the junction with the coupling member of the applicator are significantly reduced. As a result, the applicator of the present invention is of a higher reliability when compared to applicators of the prior art.

The irrigating member can also be part of a system. This system additionally includes a device, having a fluid source and a mechanism for creating a pressurized fluid stream from the fluid in the fluid source. The fluid in the fluid source is an irrigation composition, typically including bactericides, disinfectants and the like.

BRIEF DESCRIPTION OF THE DRAWINGS

The present invention will be described with reference to the accompanying drawings wherein like reference numerals indicate corresponding or like components.

In the drawings:

FIG. 1 is a side elevational view of the present invention in use;

FIG. 2 is a perspective view of the present invention in use;

DETAILED DESCRIPTION OF THE DRAWINGS

Figure 3:
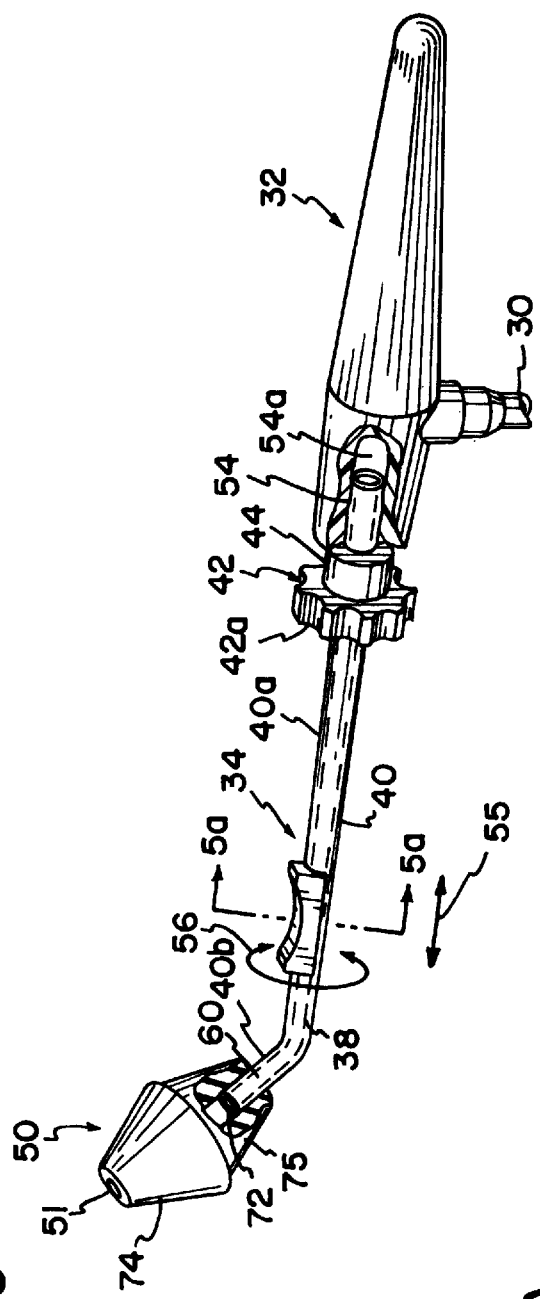
FIG. 3 is a perspective view of the present invention.

FIG. 1 shows a user 20 irrigating his nasal passages with the system of the present invention. The user 20 is preferably oriented with his body bent in a downward position so that his head 22, and in particular his nose 23, is over a conventional basin 24. A device 26, including a fluid source 27 (reservoir), feeds fluid from this source to a flexible hose 30, preferably in a pulsatile mode and under sufficient pressure, to a connecting piece 32, to which an applicator 34 connects. The user 20 places this applicator 34 proximate the nasal passage, so as to inject this pressurized pulsatile fluid stream into the nose 23, through the nostril. The device 26 (as well as the flexible hose 30 and connecting piece 32) are conventional, and for example commercially available as WATER PIK® oral irrigator(s), from Teledyne Water Pik, 1730 East Prospect Road, Ft. Collins, Colo. 80553. Other similar fluid delivery devices, such as that shown in U.S. Pat. No. 3,227,158 (Mattingly) are also suitable with the present invention.

Referring to FIG. 2, the present invention is shown in use greater detail. The user 20 is shown grasping the applicator 34 with the fingers of his left hand. While this left hand usage is shown, the applicator 34 is universal, and could also be used in the right hand in accordance with the description herein.

The user 20 preferably places his index finger 35, into contact with an opening 38 (FIG. 3) in the tube 40 of the applicator 34. The rear portion of the hand of the user 20 may clutch the applicator 34 around a grip portion 42 (FIG. 3) of a coupling member 44 (FIG. 3). A thumbrest 48, configured to receive the thumb 49 of the user 20, is slidably and preferably also rotatably connected to the tube 40 of the applicator 34. It is preferred that the user 20 position the thumbrest 48 at a point proximate to the opening 38 in the tube 40. With the thumb 49 in the thumbrest 48, that is positioned proximate the opening 38 (along the upper portion of the tube 40), the index finger 35 naturally follows the thumb 49, to a point where the index finger 35 can be easily placed into and out of contact with the opening 38, such that the user 20 controls the therapy, by controlling the fluid stream to the nose and nasal passages, on the applicator 34 itself.

When the opening 38 is covered, fluid moves through the applicator 34 and exits the applicator 34 through a fitting 50 at an outlet port 51, into the nose, so as to enter the nasal passages. When the opening 38 is uncovered, fluid can exit the applicator 34 in a controlled manner, for example, into the basin 24, and dependent on the fluid pressure, through the outlet port 51. Additional control of the fluid stream through the applicator 34 can be achieved by partially covering/uncovering the opening 38 to the degree desired, in accordance with that detailed immediately above.

It is preferred that the user's index finger 35 cover and uncover the opening 38, for it is in a natural coordination with the thumb 49, giving rise to the cooperative positioning of the index finger 35 and thumb 49 on the applicator 34. This cooperative positioning is also preferred for it also allows the user the greatest amount of control and maneuverability of the applicator 34 for placement proximate to and into the nose 23. Moreover, this cooperative positioning, with its placement of the index finger 35 and thumb 49 along the tube 40, reduces torque on the tube 40, when the applicator 34 is placed into contact with the nose, and thus, reduces the possibility of tube breakage, and in particular, tube breakage at the junction with the coupling member 44 (FIG. 3) of the applicator 34.

Alternately, the user may hold the applicator 34 such that the other fingers, including the thumb 49, are placed into and out of contact with the opening 38. However, the control of the applicator 34 is less than with the index finger 35 contacting the opening 38 and the thumb 49 in the thumbrest 48, as is preferred. Moreover, should the thumb 49 be placed into contact with the opening 38, the index finger 35 or other finger could be placed on the thumbrest 48, to better control the applicator 34.

Turning to FIG. 3, the flexible hose 30 attaches to the connecting piece 32, that in turn, couples with the applicator 34. These elements are constructed and arranged to define a pathway for the fluid stream from the device 26, particular the fluid source 27 or reservoir thereof, to the nose 23. The applicator 34 couples to the connecting piece 32 in a detachable manner, as the connecting piece 32 frictionally engages a coupler 54 of the coupling member 44 in a male-female fit.

The applicator 34 is configured such that the coupling member 44 receives and attaches to one end of the tube 40, along a straight portion 40a, while the opposite end of the tube 40 is attached to the fitting 50, along a bent portion 40b, preferably by a friction fit. The thumbrest 48 slidably engages the tube 40, such that it is movable along the length of the straight portion 40a of the tube 40 (in the direction of the double headed arrow 55), and rotatable around the straight portion 40a (in the direction of the double headed arrow 56).

The coupling member 44 is preferably integral, formed of plastic, such as ABS plastic or the like, with its fingergrip portion 42 and coupler 54 portions. The grip portion 42 is preferably of larger diameter that the remainder of the coupling member 44 and includes ridges and grooves along its outer edge 42a to facilitate gripping by the user 20. This grip portion 42 includes an inner area configured to receive the tube 40, in either a friction fit or with the assistance of adhesives or other well known fasteners. A tip 54a is preferably narrowed (tapered inward) to increase pressure of the fluid stream.

Figure 4A:
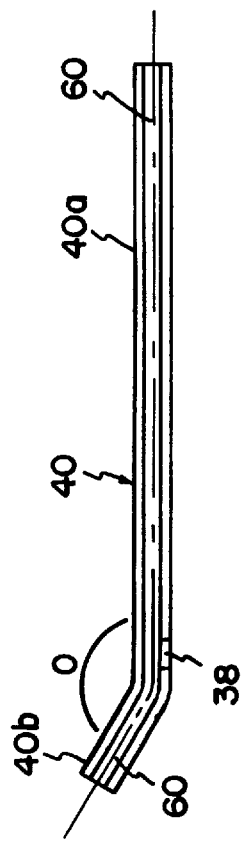
FIG. 4a is a cross-sectional view of a portion of the present invention.
Figure 4B:
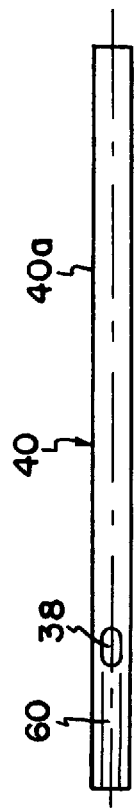
FIG. 4b is a bottom view of a portion of the present invention.

Turning also to FIGS. 4a and 4b, the tube 40, has its straight portion 40a offset from its bent portion 40b at an angle (θ), preferably between approximately 90–180 degrees, more preferably between approximately 100–170 degrees, and most preferably between approximately 115–155 degrees. The tube 40 has a central bore 60 that serves as the fluid passageway. The opening 38 extends to the bore 60, and thus, allows fluid pressure to be user controlled (detailed above), when the opening 38 is covered and uncovered.

The tube 40 is preferably made of a transparent polymeric or plastic material such as PVC, clear plastic or the like, and preferably has a central bore 60 of a uniform diameter, this central bore diameter defining the inner diameter of the tube 40. For example, the tube 40 can have a typical inner diameter of approximately 0.094 inches and a typical outer diameter of approximately 0.196 inches.

The opening 38 is substantially oval in shape, but other shapes, such as rectangular, circular, triangular combinations therof or the like are also permissible. The opening 38 sized such that it can be completely covered by the index finger 35 (FIG. 2) (or alternately, other fingers or thumb 49) of the user 20.

Figure 5B:
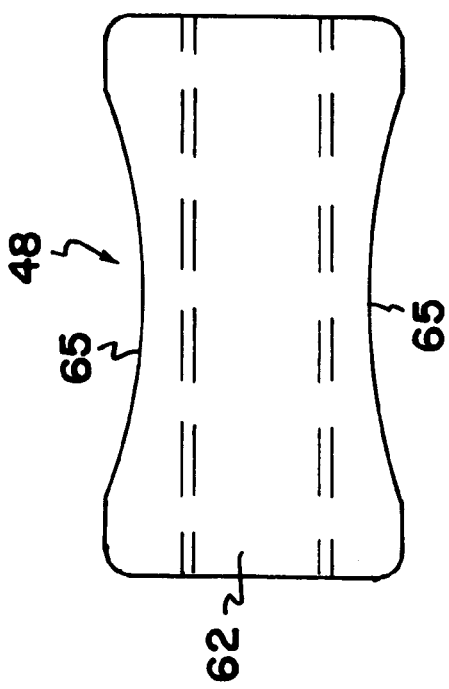
FIGS. 5b and 5c are bottom and side views respectively of a portion of the present invention.
Figure 5C:
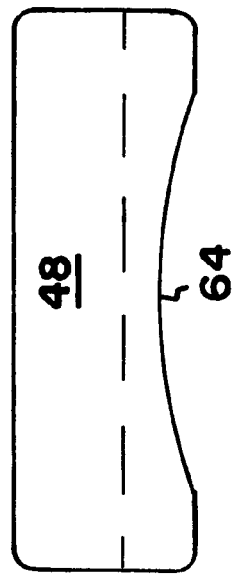
Figure 5A:
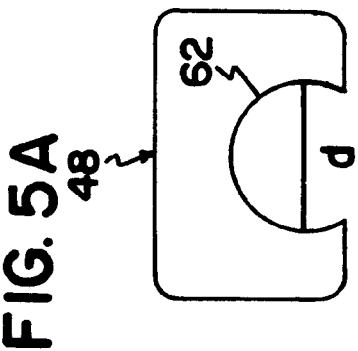
FIG. 5a is a cross-sectional view of a portion of the present invention taken along line 5a—5a of FIG. 3.

The thumbrest 48, shown in detail in FIGS. 5a–5c, is preferably a separate piece that is snapped or otherwise frictionally attached onto the tube 40, to form a slidable engagement with the tube 40, by virtue of a friction fit. The friction fit is of sufficient force, such that the thumbrest 48 can be maintained in the desired position, until forcibly moved. The friction fit (and slidable engagement) is achieved by configuring the tube receiving portion 62 to be of an arc length preferably slightly greater than semicircular with a diameter "d" to be slightly less than that of the outer diameter of the tube 40. The thumbrest 48 also includes a groove 64, dimensioned to accommodate the thumb 49, when placed thereon, as well as lateral grooves 65. It is preferred that the thumbrest 48 be made of polymeric or plastic materials, such as DELRIN® (E. I. DuPont de Nemours and Company, Wilmington, Del.), acetal or the like.

Turning back to FIG. 3, the fitting 50 attaches to the tube 40 so that its internal bore 72 aligns with the corresponding bore 60 of the tube 40. The fitting 50 is of two portions, upper and lower, 74, 75, preferably conical in shape. The upper portion 74 is of a diameter larger than the nostril, to serve as a limit of travel for the applicator 34. The lower portion 75 is of an internal diameter to frictionally engage the bent portion 40b of the tube 40. Should additional securement of the fitting 50 to the tube 40 be desired, adhesives or other well known fasteners are also permissible. It is preferred that the tapering of the upper portion 74 be at angles (with respect to the vertical) of approximately 10–50 degrees, with an angle of approximately 25 degrees preferred. The fitting is preferably made of rubber, polymeric material, such as PVC or the like, by conventional manufacturing techniques.

In use, as shown and described in FIGS. 1 and 2 above, and also with reference to FIGS. 3–5c above, the fluid source 27 (or reservoir) of the device 26 is filled with an irrigation solution, preferably at approximately room temperature or slightly below. The irrigation solution preferred is a 3 wt-% saline solution disclosed in a commonly assigned U.S. Patent Application, entitled: HYPERTONIC SALINE SOLUTION, incorporated by reference in its entirety herein. Other irrigation solutions may also be used.

The device 26 is then activated to be in a pulsatile mode, with approximately 500–1500 pulses (cycles) per minute, and preferably approximately 1200 pulses per minute, at pressures of not greater than approximately 2–7 psi, and preferably approximately 5 psi. The user 20 then places his thumb 49 on the thumbrest 48 and slides the thumbrest 48 into position, preferably along the upper portion of the tube 40. The user then places his index finger 35 over the opening 38 and places the fitting 50 into proximity with the nostril, and preferably into contact therewith (and preferably assumes the downwardly bent position shown in FIG. 1 over a basin 24 or the like). Fluid irrigation into the nasal passages continues as desired, and should it be desired that irrigation pressure be temporarily or permanently lowered, the index finger 35 may be moved, such that the opening 38 is fully or partially uncovered, and fluid can exit the applicator 34 in a controlled manner, e.g., into the basin 24, without the user 20 having to reach for the device 26 (to control fluid flow or shut off fluid flow completely). Nasal irrigation continues until the fluid in the device is exhausted.

While the present invention has been described above so as to enable one skilled in the art to practice it, the preceding description is exemplary only, and should not be used to limit the scope of the invention. The scope of the invention should be defined by the following claims.

What is claimed is:

1. An irrigating member comprising:
    a tubular member having a bore extending therethrough, said tubular member including a first portion and a second portion offset from each other at an angle; said tubular member adapted for receiving a pressurized stream of fluid from a fluid source;
    an opening in said first portion of said tubular member, said opening in communication with said bore; and
    a thumbrest slidably connected to said first portion of said tubular member.

2. The irrigating member of claim 1, additionally comprising a fitting member for contact with a nose, said fitting member including at least one portion of a diameter greater than the diameter of the nostril of the nose.

3. The irrigating member of claim 1, wherein said offset angle is approximately 150°.

4. A nasal irrigation system comprising:
    a fluid source;
    means in communication with said fluid source for creating a pressurized fluid stream; and
    an irrigating member in communication with said pressurized fluid stream creating means, said irrigating member comprising:
        a tubular member having a bore extending therethrough, said tubular member including a first portion and a second portion offset from each other at an angle; said tubular member adapted for receiving a pressurized stream of fluid from a fluid source; and
        an opening in said first portion of said tubular member, said opening in communication with said bore; and
        a thumbrest slidably connected to said first portion of said tubular member.

5. The system of claim 4, additionally comprising a fitting member for contact with a nose, said fitting member including at least one portion of a diameter greater than the diameter of the nostril of the nose.

6. The system of claim 4, wherein said offset angle is approximately 150°.

7. A method for irrigating a nasal passage comprising:
    providing a source of nasal irrigation fluid;
    providing a system for moving said nasal irrigation fluid in a pressurized stream, said system comprising,
        a tubular member having a bore extending therethrough, said tubular member including a first portion and a second portion offset from each other at an angle; said tubular member adapted for receiving a pressurized stream of fluid from a fluid source; and
        an opening in said first portion of said tubular member, said opening in communication with said bore;
    placing said tubular member at least proximate to the nose and activating said system; and
    controlling the pressure of said stream by covering and uncovering said opening; and
    a thumbrest slidably connected to said first portion of said tubular member.

8. A nasal irrigation system comprising:
    a fluid source, said fluid source including an intranasal buffered hypertonic solution consisting of:
        a. 3 wt % sodium chloride;
        b. 0.095 wt-% potassium phosphate;
        c. 1.260 wt-% sodium phosphate; and
        d. the balance being water;
    means in communication with said fluid source for creating a pressurized fluid stream; and
    an irrigating member in communication with said pressurized fluid stream creating means, said irrigating member comprising:
        a tubular member having a bore extending therethrough, said tubular member including a first portion and a second portion offset from each other at an angle; said tubular member adapted for receiving a pressurized stream of fluid from a fluid source; and an opening in said first portion of said tubular member, said opening in communication with said bore; and a thumbrest slidably connected to said first portion of said tubular member.

9. The irrigating member of claim 8, additionally comprising a fitting member for contact with a nose, said fitting member including at least one portion of a diameter greater than the diameter of the nostril of the nose.

10. The irrigating member of claim 8, wherein said offset angle is approximately 150°.

11. A nasal irrigation system comprising:

a fluid source, said fluid source including an intranasal buffered hypertonic solution consisting of a 3 wt % sodium chloride at a pH of approximately 7.6;

means in communication with said fluid source for creating a pressurized fluid stream; and an irrigating member in communication with said pressurized fluid stream creating means, said irrigating member comprising:

a tubular member having a bore extending therethrough, said tubular member including a first portion and a second portion offset from each other at an angle; said tubular member adapted for receiving a pressurized stream of fluid from a fluid source; and an opening in said first portion of said tubular member, said opening in communication with said bore; and a thumbrest slidably connected to said first portion of said tubular member.

12. The irrigating member of claim 11, additionally comprising a fitting member for contact with a nose, said fitting member including at least one portion of a diameter greater than the diameter of the nostril of the nose.

13. The irrigating member of claim 11, wherein said offset angle is approximately 150°.

14. A method for irrigating a nasal passage comprising:

providing a source of nasal irrigation fluid, said nasal irrigation fluid comprising, a buffered hypertonic solution consisting of a 3 wt % sodium chloride at a pH of approximately 7.6;

providing a system for moving said nasal irrigation fluid in a pressurized stream, said system comprising, a tubular member having a bore extending therethrough, said tubular member including a first portion and a second portion offset from each other at an angle; said tubular member adapted for receiving a pressurized stream of fluid from a fluid source; and an opening in said first portion of said tubular member, said opening in communication with said bore;

placing said tubular member at least proximate to the nose and activating said system; and controlling the pressure of said stream by covering and uncovering said opening; and a thumbrest slidably connected to said first portion of said tubular member.

15. The method of claim 14, wherein said solution additionally comprises:

0.095 wt-% potassium phosphate;

1.260 wt-% sodium phosphate; and the balance being water.

\* \* \* \* \*